United States Patent
Kondo et al.

(10) Patent No.: US 8,500,846 B2
(45) Date of Patent: Aug. 6, 2013

(54) RARE METAL EXTRACTANT

(75) Inventors: Yoshihiko Kondo, Akita (JP); Chun-bin Li, Akita (JP); Manabu Yamada, Akita (JP); Fumio Hamada, Akita (JP)

(73) Assignee: Akita University, Akita-shi, Akita (JP)

(*) Notice: Subject to any disclaimer, the term of this patent is extended or adjusted under 35 U.S.C. 154(b) by 337 days.

(21) Appl. No.: 12/866,602

(22) PCT Filed: Feb. 10, 2009

(86) PCT No.: PCT/JP2009/052198
§ 371 (c)(1),
(2), (4) Date: Aug. 6, 2010

(87) PCT Pub. No.: WO2009/101926
PCT Pub. Date: Aug. 20, 2009

(65) Prior Publication Data
US 2011/0011215 A1    Jan. 20, 2011

(30) Foreign Application Priority Data
Feb. 12, 2008  (JP) ................................. 2008-031127

(51) Int. Cl.
*C22B 3/16*  (2006.01)
*C01F 7/00*  (2006.01)

(52) U.S. Cl.
USPC ................ 75/711; 75/721; 423/22; 423/70

(58) Field of Classification Search
USPC .................................................. 75/711, 721
See application file for complete search history.

(56) References Cited

U.S. PATENT DOCUMENTS
8,038,969 B2 * 10/2011 Kondo et al. ................ 423/22

FOREIGN PATENT DOCUMENTS

| JP | 10-175971 A | 6/1998 |
| JP | 11-152284 A | 6/1999 |
| JP | 11-179104 A | 7/1999 |
| JP | 2000-107505 A | 4/2000 |
| JP | 2003-507359 A | 2/2003 |
| JP | 2005-061970 A | 3/2005 |
| JP | 2005-061971 A | 3/2005 |
| JP | 2007-239066 A | 9/2007 |
| JP | 2007-239088 A | 9/2007 |
| WO | 01/12586 A1 | 2/2001 |

OTHER PUBLICATIONS

International Search Report: PCT/JP2009/052198.

* cited by examiner

*Primary Examiner* — George Wyszomierski
*Assistant Examiner* — Tima M McGuthry Banks
(74) *Attorney, Agent, or Firm* — Ladas & Parry LLP

(57) ABSTRACT

The present invention is to provide a novel rare metal extractant containing a cyclic phenol sulfide derivative of the formula (1) and a method for extractive separation of rare metal(s) using the rare metal extractant with high efficiency.

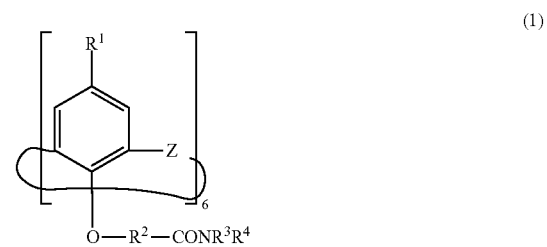

12 Claims, 2 Drawing Sheets

RARE METAL EXTRACTANT

TECHNICAL FIELD

The present invention provides a novel rare metal extractant and a method for extractive separation of rare metals using the extractant.

BACKGROUND ART

Rare metals (for example, cobalt (Co), titanium (Ti), vanadium (V), chromium (Cr), manganese (Mn), zinc (Zn), yttrium (Y), zirconium (Zr), niobium (Nb), cadmium (Cd), lanthanum (La), cerium (Ce), neodymium (Nd), europium (Eu), terbium (Tb), mercury (Hg), uranium (U), platinum (Pt), palladium (Pd), rhodium (Rh), ruthenium (Ru), iridium (Ir), and osmium (Os)) are essential for our daily life. These metals are used in various products including modern precision equipment such as catalyst for automobile, fuel cell, and ultrahigh-strength magnet. Japan has been heavily dependent on imports for these metals; so, in view of stable supply of resources and environmental protection, recycle of these rare metals is an important technology.

For recycling of rare metals, conventionally, various solvent extraction methods from rare-metal-containing aqueous solution have been used and various extractants have been developed and used. For example, Patent documents 1 and 2 disclose that cyclic phenol sulfides having particular structures are useful as rare metal extractants and they are effective to selectively extract rare metal(s).

Patent Document 1: Japanese Patent Application Laid-Open (JP-A) No. 2007-239066
Patent Document 2: JP-A No. 2007-239088

DISCLOSURE OF THE INVENTION

Problems to be solved by the Invention

Nevertheless, the rare-metal-containing aqueous solution is obtained by extracting rare metals with various acids from various waste products. Therefore, the concentration and species of metals as well as impurities contained in rare-metal-containing aqueous solution are of great variety. To selectively and efficiently extract plural species of particular rare metals from a solution containing various species of rare metals, it is necessary to perform multi-step extraction with a combination of various extractants such as that shown in Patent documents 1 and 2, which results in a time-consuming and expensive extraction process.

Accordingly, an object of the present invention is to provide a novel rare metal extractant, and a method for extractive separation of rare metals using the extractant with efficiency.

Means for Solving the Problems

The present inventors discovered that particular rare metal (s) can be efficiently extracted and separated by using a compound having a particular structure as an extractant, and the effect of extractive separation can be significantly changed depending on the kind of rare metal by slightly changing the pH of the solution; then, they completed the present invention.

The first aspect of the present invention is a rare metal extractant containing a cyclic phenol sulfide derivative of the formula (1):

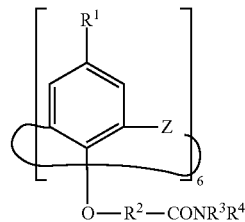

(Formula 1)

(in the formula (1), $R^1$, $R^3$, and $R^4$ are independently a hydrogen atom or a $C_1$-$C_{10}$ hydrocarbon; $R^2$ is a $C_0$-$C_{10}$ hydrocarbon; and Z is any one of a sulfide group, a sulfinyl group, and a sulfonyl group.)

It should be noted that the term "rare metal" means a generic name of rare species of metal; the "rare metal" in this description includes: platinum (Pt), palladium (Pd), rhodium (Rh), ruthenium (Ru), iridium (Ir), and osmium (Os), cobalt (Co), titanium (Ti), vanadium (V), chromium (Cr), manganese (Mn), zinc (Zn), yttrium (Y), zirconium (Zr), niobium (Nb), cadmium (Cd), lanthanum (La), cerium (Ce), neodymium (Nd), europium (Eu), terbium (Tb), mercury (Hg), and uranium (U).

In the first aspect of the invention, in the formula (1), preferably, $R^1$, $R^3$, and $R^4$ are independently a hydrogen atom or a linear or branched $C_1$-$C_{10}$ alkyl group; and $R^2$ is a $C_0$-$C_{10}$ alkylene group.

The second aspect of the present invention is a method for consecutive extractive separation of plural species of rare metals with a rare metal extractant containing a cyclic phenol sulfide derivative of the formula (1) from an aqueous solution containing plural species of rare metals, comprising the step of: extracting rare metal repeatedly by changing pH of the aqueous solution more than once depending on a desired rare metal, to selectively dominantly extract particular rare metal(s).

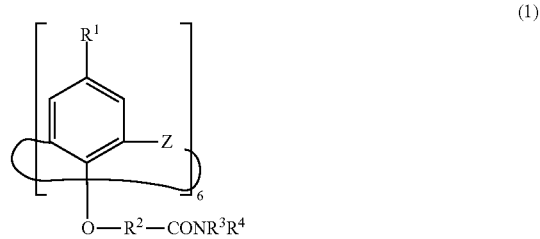

(in the formula (1), $R^1$, $R^3$, and $R^4$ are independently a hydrogen atom or a $C_1$-$C_{10}$ hydrocarbon; $R^2$ is a $C_0$-$C_{10}$ hydrocarbon; and Z is any one of a sulfide group, a sulfinyl group, and a sulfonyl group.)

In the second aspect of the invention, the pH to be changed more than once preferably includes ranges of more than 0.8 and less than 1.2 and/or more than 1.2 and less than 1.8.

The third aspect of the present invention is a method for consecutive extractive separation of plural species of rare metals, comprising the steps of: extracting rare metal with a rare metal extractant containing a cyclic phenol sulfide derivative of the formula (1) from an aqueous solution containing plural species of rare metals; and extracting rare metal with a rare metal extractant containing a rare metal extractant which contains a thiacalixarene other than the compound of the formula (1) from an aqueous solution containing plural species of rare metals, to selectively dominantly extract particular rare metal(s) in each step.

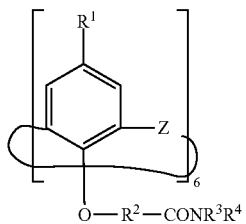

(1)

(in the formula (1), $R^1$, $R^3$, and $R^4$ are independently a hydrogen atom or a $C_1$-$C_{10}$ hydrocarbon; $R^2$ is a $C_0$-$C_{10}$ hydrocarbon; and Z is any one of a sulfide group, a sulfinyl group, and a sulfonyl group.)

In the third aspect of the invention, the rare metal extractant which contains a thiacalixarene other than the compound of formula (1) is preferably a rare metal extractant containing a thiacalixarene of the formula (2).

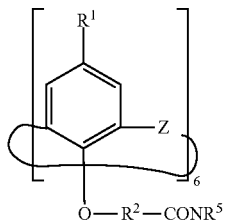

(2)

(in the formula (2), $R^1$ and $R^5$ are independently a hydrogen atom or a $C_1$-$C_{10}$ hydrocarbon; $R^2$ is a $C_0$-$C_{10}$ hydrocarbon; and Z is any one of a sulfide group, a sulfinyl group, and a sulfonyl group.)

In the second and the third aspect of the invention, one of the extracting steps is preferably a step to selectively dominantly extract platinum.

Effects of the Invention

By the rare metal extractant according to the first aspect of the invention and the method for consecutive extractive separation of plural species of rare metals according to the second aspect of the invention, during extractive separation of rare metals from waste products and waste liquid, it is possible to efficiently extract and separate plural species of rare metals by only changing pH of the solution with single extractant. Because of this, the number of the steps of extractive separation can be reduced, thereby the extraction can be performed at a low cost; hence, it is possible to facilitate recycling of rare metals.

By the method for consecutive extractive separation of plural species of rare metals according to the third aspect of the invention, by using a combination of the extractant of the first aspect of the invention and the extractant containing a thiacalixarene other than the cyclic phenol sulfide derivative of the first aspect of the invention, it is possible to consecutively extract plural species of rare metal, and it is also possible to extract and remove unwanted metal(s) in the first step and then to extract the desired rare metal with high efficiency in the second step.

BEST MODE FOR CARRYING OUT THE INVENTION

Rare Metal Extractant

Figure 1:
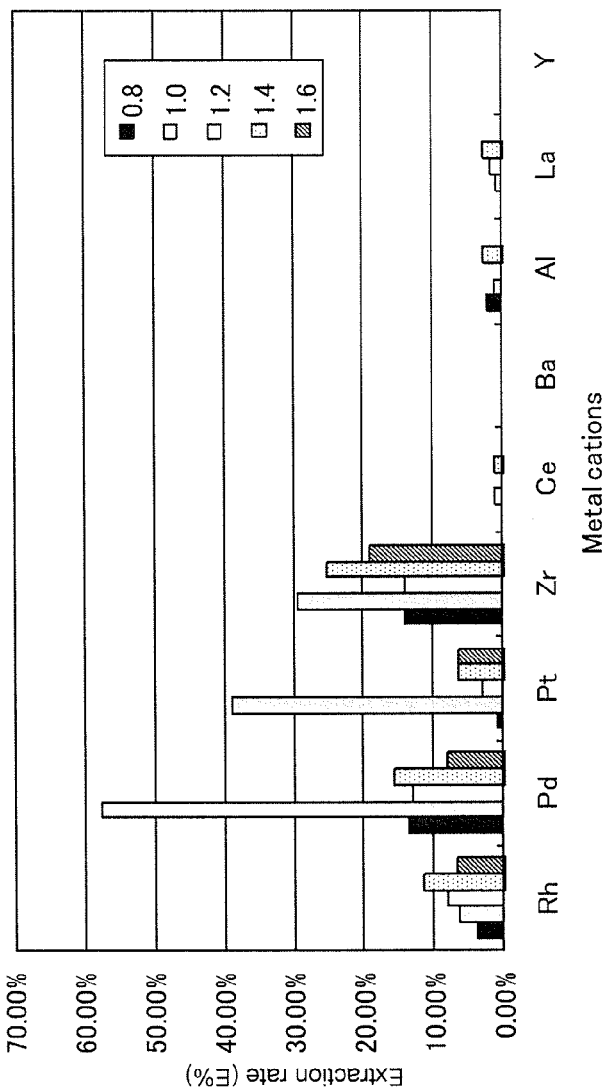
FIG. 1 is a graph showing the result of experiment for extractive separation of rare metals according to Example 1.

The rare metal extractant of the present invention is the one containing a cyclic phenol sulfide derivative of the formula (1).

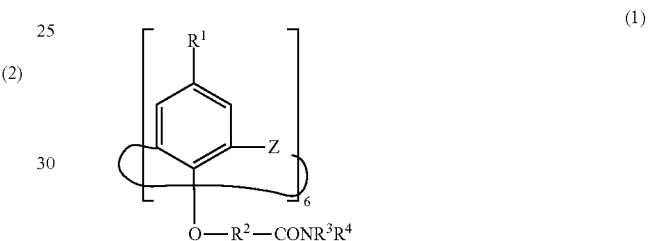

(1)

In the formula (1), —$CONR^3R^4$ is a substituted carbamoyl group; $R^1$, $R^3$ and $R^4$ are independently a hydrogen atom or a $C_1$-$C_{10}$ hydrocarbon. As $R^1$, $R^3$, and $R^4$, a hydrogen atom or a linear or branched alkyl group is preferable; specific examples of the alkyl group include: methyl, ethyl, n-propyl, isopropyl, n-butyl, isobutyl, t-butyl, n-pentyl, and n-hexyl. In the formula (1), $R^2$ is a $C_0$-$C_{10}$ hydrocarbon; it is preferably a linear or branched alkylene group specifically including: methylene, ethylene, n-propylene, isopropylene, n-butylene, t-butylene, s-butylene, n-pentylene, and n-hexylene. Here, $C_0$ hydrocarbon as $R^2$ means the situation that there is no substituent equivalent to $R^2$ in the formula (1) thereby the oxygen atom and the carbon atom of the carbonyl group both of which adjacent to $R^2$ are directly bound each other.

More specifically, $R^1$ is preferably a hydrogen atom or a linear or branched $C_1$-$C_{10}$ alkyl group; among them, a linear or branched $C_3$-$C_5$ alkyl group is preferable. $R^2$ is preferably a linear or branched $C_0$-$C_5$ alkylene group; among them, methylene and ethylene groups are preferable. $R^3$ and $R^4$ are preferably independently a hydrogen atom or a linear or branched $C_1$-$C_5$ alkyl group; among them, methyl, ethyl, and propyl groups are preferable.

Z is any one of a sulfide group, a sulfinyl group, and a sulfonyl group.

The compound of the formula (1) has a structure where six phenol derivative skeletons are circularly-connected through Z; the substituent $R^1$, $R^2$, $R^3$, and $R^4$ included in each of the six phenol derivative skeletons may be the same or different, and the six Z may be the same or different. In view of ease of manufacturing and extractive property of the obtained compound for the rare metals, $R^1$, $R^2$, $R^3$, and $R^4$ included in each of the six phenol derivative skeletons may preferably be the same and the six Z may also preferably be the same.

The cyclic phenol sulfide derivative of the formula (1) can be synthesized by a known method. For example, the cyclic phenol sulfide derivative can be obtained by: selecting, as a starting material, an alkyl phenol of which 4-position is substituted by $R^1$; reacting the alkyl phenol with elemental sulfur in the presence of alkali metal reagent or alkali-earth metal reagent so as to obtain a cyclic phenol sulfide where six of alkyl phenols are circularly-connected by sulfide bonds; and then substituting the respective hydrogen atom of the phenolic hydroxy group with carbamoyl groups each having $R^2$, $R^3$, and $R^4$. Examples of the reagents of alkali metal and of alkali-earth metal to be used during the synthesis of the cyclic phenol sulfide, include: elemental metal, hydride, halide, oxide, carbonate, and alkoxide. Examples of the method for substituting the respective hydrogen atom of the phenolic hydroxy groups with the carbamoyl groups may be a method that the carbamoyl alkyl halide having $R^2$, $R^3$, and $R^4$ is directly reacted with phenolic hydroxyl group under basic conditions, or a method comprising the steps of: substituting the hydrogen atom of the phenolic hydroxy group with an alkali metal; reacting the substituted portion with alkoxycarbonyl alkyl halide; hydrolyzing the ester moiety to obtain a carboxyalkyl group; converting the resultant compound into an acid chloride, and finally reacting the acid chloride with an amine. Sulfide group of the cyclic phenol sulfide, namely Z of the formula (1) can be converted into a sulfinyl group or a sulfonyl group, as required, by oxidation using an oxidant such as hydrogen peroxide or sodium perborate.

The cyclic phenol sulfide derivatives of the formula (1) can be suitably used as rare metal extractant for extracting rare metals from a rare-metal-containing solution. The cyclic phenol sulfide derivative of the formula (1) is usually dissolved in a solvent to afford a solution; by bringing the solution (hereinafter, referred to as "solution of rare metal extractant".) into contact with a solution in which rare metals are dissolved (hereinafter, referred to as "rare-metal-dissolved solution".), the rare metals dissolved in the rare-metal-dissolved solution are transferred to the solution of rare metal extractant; thus the rare metals are extracted. As the solvent to be used for the solution of rare metal extractant and the solvent to be used for the rare-metal-dissolved solution, solvents which are hardly soluble with each other are used. The solvent to be used for each solution may be a mixture of two or more solvents. The solvents may particularly preferably be a combination of a non-aqueous solvent as the solvent for the solution of rare metal extractant and water as the solvent for the rare-metal-dissolved solution.

The non-aqueous solvent is not particularly limited as long as it can dissolve the cyclic phenol sulfide derivative of the formula (1). Examples thereof include: a mineral oil such as petroleum oil and kerosene; an aliphatic hydrocarbon such as hexane, heptane, and octane; an aromatic hydrocarbon such as toluene and xylene; and a halogenated solvent such as carbon tetrachloride, methylene chloride, chloroform, and ethylene chloride.

The concentration of the cyclic phenol sulfide derivative of the formula (1) in the solution of rare metal extractant is not particularly limited except for the upper limit restricted by the solubility of the cyclic phenol sulfide derivative. If the concentration is too low, rare metal extraction effect cannot be obtained; therefore, the concentration is usually in the range of $1 \times 10^{-6}$ M to 1 M. The concentration of rare metals in the rare-metal-dissolved aqueous solution is not particularly limited; it is usually about 1000 ppm.

<Method for Consecutive Extractive Separation of Plural Species of Rare Metals According to the Second Aspect of the Invention>

In the extraction of rare metal using the rare metal extractant of the present invention, by changing pH of the rare-metal-dissolved solution, extraction rate of the rare metal varies; the variation of the extraction rate significantly differs among the metal species. Therefore, if pH of the rare-metal-dissolved solution is set at a pH at which the desired metal species can be extracted best, the particular rare metal can be selectively dominantly extracted; thereby rare metals can be efficiently extracted. Moreover, in a case of extracting plural species of rare metals from the rare-metal-dissolved solution, by consecutively repeating: extracting one species of metal by setting pH of the rare-metal-dissolved solution at a pH at which the metal can be extracted best; and then extracting other species of metal by re-setting the rare-metal-dissolved aqueous solution at a pH at which each of other species of metals can be extracted best, it is possible to efficiently extract plural species of rare metals one after another with one rare metal extractant. For instance, by adjusting pH in the range of more than 0.8 and less than 1.2, Pd and/or Pt can be selectively extracted. In addition, by adjusting pH in the range of more than 1.2 and less than 1.8, Zr can be selectively extracted.

The pH of the rare-metal-dissolved solution can be adjusted to be the selected pH by adding acid or base. The acid and base may be conventional ones used for adjusting pH. Examples of the acid include: sulfuric acid, hydrochloric acid, nitric acid, and acetic acid; examples of the base include: sodium hydroxide, potassium hydroxide, and calcium hydroxide. The pH range adjusted during extraction is usually about 0 to 7; in view of extraction rate, pH in the range of 1 to 5 is preferable.

The extraction temperature is not particularly limited as long as it is the boiling point or less of the solvent to be used; extraction is usually carried out at around room temperature. The extraction operation is carried out by bringing the solution of rare metal extractant into contact with the rare-metal-dissolved solution by shaking or stirring. The conditions of shaking and stirring are not particularly limited; shaking may usually be performed about 60 to 200 times per minutes.

In view of extraction efficiency, the rare metal extractant of the present invention is effective for extraction of zirconium (Zr), palladium (Pd), and platinum (Pt) among rare metals, and it is particularly effective for extraction of platinum (Pt).

<Consecutive Extractive Separation of Plural Species of Rare Metals According to the Third Aspect of the Invention>

When the step of extracting rare metal (s) with the rare metal extractant of the first aspect of the invention is combined with at least one extraction step using an extractant containing a thiacalixarene other than the extractant of the first aspect of the invention, it is possible to selectively dominantly extract a particular rare metal from the aqueous solution containing plural species of rare metal in each extraction step.

By using the plural kinds of extractants in combination, plural species of rare metals can be consecutively extracted one after another. Moreover, by using the plural kinds of extractants in combination, it is possible to remove the unwanted metal components by extraction in the first step, and then extract the desired rare metal with high efficiency in the second step.

The extractant other than the extractant of the first aspect of the invention, namely, the rare metal extractant containing a thiacalixarene other than the compound of the formula (1) may be a rare metal extractant containing a thiacalixarene of the formula (2).

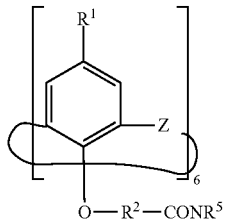

(In the formula (2), $R^1$ and $R^5$ are independently a hydrogen atom or a $C_1$-$C_{10}$ hydrocarbon; $R^2$ is a $C_0$-$C_{10}$ hydrocarbon; and Z is any one of a sulfide group, a sulfinyl group, and a sulfonyl group.)

The $R^1 R^2$, and Z of the formula (2) are the same as those of the formula (1). The $R^5$ is independently a hydrogen atom or a $C_1$-$C_{10}$ hydrocarbon; among them, $R^5$ is preferably a hydrogen atom, in other words, the compound of the formula (2) preferably has a carboxy group. Alternatively, the $R^5$ is preferably a $C_1$-$C_5$ hydrocarbon, more preferably a $C_1$-$C_4$ hydrocarbon, and most preferably a $C_1$-$C_3$ hydrocarbon; namely, the compound of the formula (2) preferably has an ester group.

One preferable mode of the consecutive extractive separation of plural species of rare metals according to the third aspect of the invention comprises the steps of: a first step for selectively extracting Pd and Zr with a rare metal extractant containing a thiacalixarene of the formula (2); and then, a second step for selectively extracting Pt with the rare metal extractant containing the cyclic phenol sulfide derivative of the formula (1) from the aqueous solution from which Pd and Zr have been removed. According to the method, it is possible to easily isolate expensive platinum with high efficiency.

EXAMPLES

Hereinafter, the present invention will be more specifically described by way of the following examples. However, the invention is not limited to the examples.

First Example

Production Example 1

Production of Cyclic Phenol Sulfide Intermediate (Oligomer A)

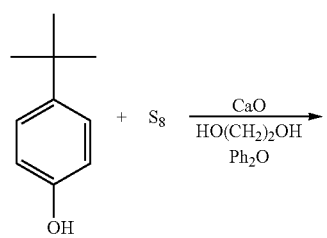

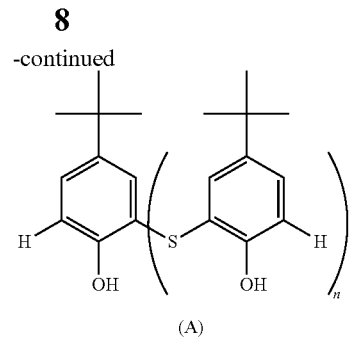

(A)

A 1000 mL three-neck flask was charged with: 300 g (2.0 mol) of p-tert-butylphenol, 64.0 mL of diphenyl ether, and 56.0 mL (1.0 mol) of ethylene glycol; and the mixture was heated with stirring under nitrogen atmosphere. When the temperature reached 60° C., 28.0 g (0.5 mol) of calcium oxide was added; the temperature was raised up to 120° C. in about 20 minutes and then the mixture was reacted for 2 hours. After the reaction, ethylene glycol and water produced by the reaction were removed under reduced pressure. A certain amount of diphenyl ether which was removed during the removal under reduced pressure was added and the mixture was heated with stirring again under nitrogen atmosphere. When the temperature reached 100° C., 95.9 g (3.0 mol) of sulfur was added in one portion; the temperature was raised up to 230° C. and then the mixture was reacted for 3 hours. After the reaction, the reaction solution was allowed to cool. When the temperature was confirmed to have decreased down to 110° C., 250 mL of toluene was gradually added to the reaction solution to reduce the viscosity; then, the diluted reaction solution was quenched by pouring it into a 500 mL of 4N sulfuric acid. Precipitated calcium sulfate was filtered, and the filtrate was washed with a saturated aqueous sodium sulfate solution; then, the obtained organic phase was concentrated and heated to 80° C. A separately prepared 1 L of acetic acid was heated to 80° C. and the concentrated reaction solution was poured thereto; then, the obtained mixture was stirred at 80° C. for about 1 hour and it was left standing overnight at room temperature. Precipitation was washed with distilled water; then, to remove remaining acetic acid, the precipitation was dissolved in a large amount of chloroform and the solution was washed with aqueous sodium sulfate solution. Thereafter, the organic layer was dried over anhydrous sodium sulfate and concentrated; then it was dried under reduced pressure overnight. Consequently, a cyclic phenol sulfide intermediate (oligomer A) was obtained in 67.8% yield.

Production Example 2

Production of Cyclic Phenol Sulfide (B)

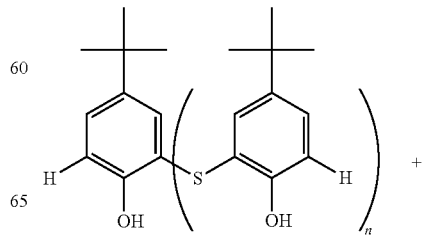

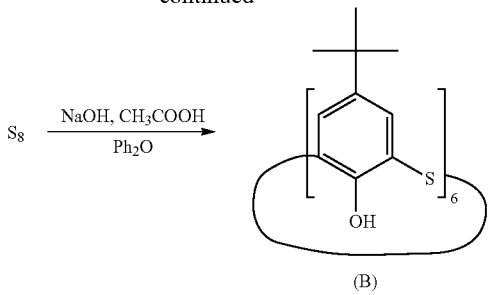

A 500 mL three-neck flask was charged with: 30 g of the cyclic phenol sulfide intermediate oligomer obtained in Production example 1, 64.0 mL of diphenyl ether, 3.99 g of sodium hydroxide, and 1.62 g of acetic acid, in the mentioned order; and the mixture was heated with stirring under nitrogen atmosphere. When the temperature reached 100° C., 2.14 g of sulfur was added in one portion; the temperature was raised up to 230° C. in about 1 hour and then the mixture was reacted for 4 hours. After the reaction, the reaction solution was allowed to cool and then quenched by pouring 100 mL of 2N sulfuric acid into the reaction solution. Next, 100 mL of n-heptane was added thereto and the mixture was stirred for about 10 minutes. Then, the mixture was washed with aqueous sodium sulfate solution to remove sulfuric acid, and the organic layer was separated. The diphenyl ether in the organic phase was removed under reduced pressure, and acetone was added to form precipitation. By filtering the precipitation and drying under reduced pressure, crude crystal of the cyclic phenol sulfide was obtained. By dissolving the crude crystal in chloroform and performing recrystallization, the cyclic phenol sulfide (B) was purified. Yield of the cyclic phenol sulfide (B) after purification was 11.4%.

Production Example 3

Production of Cyclic Phenol Sulfide Derivative (1-1)

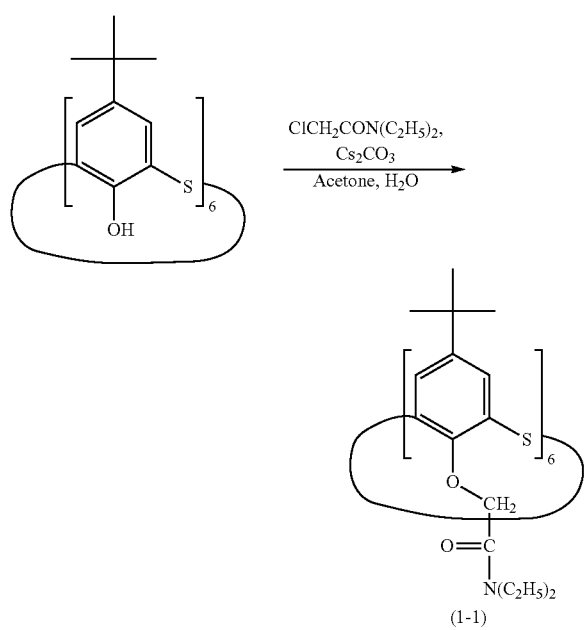

A 300 mL three-neck flask was charged with: 1.66 g of α-chloro-N,N-diethylacetamide, 1.66 g of sodium iodide, and 30 mL of acetone; and the mixture were stirred at room temperature for 2 hours. Then, to the mixture, 1.0 g of cyclic phenol sulfide (B) obtained in Production example 2, 2.67 g of cesium carbonate, 65 mL of acetone, and 5 mL of water were added and the mixture was heated with stirring at 64° C. under nitrogen atmosphere for 120 hours. After the reaction, the reaction mixture was concentrated by evaporating acetone, the residue was dissolved in chloroform, and the solution was washed with 2N hydrochloric acid twice and then washed with distilled water twice. The obtained organic layer was dried over anhydrous sodium sulfate and chloroform was evaporated. By washing the obtained residue by acetone and filtering the washed residue, the desired cyclic phenol sulfide derivative (1-1) was obtained. The yield was 78.1%.

Example 1

Extractive Separation of Rare Metal with the Cyclic Phenol Sulfide Derivative (1-1)

An experiment of rare metal extraction was conducted with the cyclic phenol sulfide derivative (1-1) obtained in the production example 3 as a rare metal extractant.

Firstly, a 200 mL separating funnel was charged with: 50 mL of organic phase obtained by dissolving the cyclic phenol sulfide derivative (1-1) in chloroform so that the concentration was 2.92 mM; and 50 mL of aqueous phase (pH: 0.8) obtained by preparing a PGM (Platinum-group Metals) solution (including: Rh=264.3 ppm, Pd=737.8 ppm, Pt=434.1 ppm, Zr=198.2 ppm, Ce>3840.5 ppm, Ba=2118.2 ppm, Al=2272.5 ppm, La=666.9 ppm, and Y=36.3 ppm) where several species of rare metals contained in the waste products discarded from factory were made into an aqueous solution by acid treatment and by diluting the PGM solution 50-fold with distilled water. Then, these were shaken and agitated for 30 minutes.

After that, the concentration of metals in the aqueous phase was analyzed by using ICP (inductively coupled plasma) emission spectrometer, and the extraction rate (E %) according to the obtained result was calculated with the following formula (I). The concentration ratio of the cyclic phenol sulfide derivative and metals in the aqueous solution were supposed to be a moler concentration ratio of 1:1:

$$(E\%) = (C_0 - C)/C_0 \times 100 \quad (I)$$

(Wherein, $C_0$ is a metal concentration of the aqueous layer before extraction (ppm), C is a metal concentration of the aqueous layer after extraction (ppm).).

Moreover, apart from this, four 50 mL samples each of which was obtained by diluting the PGM solution 50-fold with distilled water and adjusting the pH of the diluted PGM solution to be pH=1.0, 1.2, 1.4, and 1.6 with 10N sodium hydroxide aqueous solution were prepared; then, the metals of each solution were extracted in the same manner as above and the extraction rate (E %) were calculated. The extraction result is shown in FIG. 1 (it should be noted that the final results were the average of two extraction results of each sample (hereinafter, same as this.).).

As seen from the graph of FIG. 1, the extraction rate of each metal largely varies according to the pH of the PGM solution; the relation between the pH and extraction rate also varies according to the metal species. Therefore, it is possible to change the metal species to be dominantly extracted by changing the pH of the PGM solution. As a result, extraction efficiency of the desired rare metal can be enhanced. For example, according to the graph of FIG. 1, with the rare metal extractant used in Example 1, when Pd and Pt are the main target to be extracted, if the pH is adjusted at 1.0, these metals can be most efficiently extracted; while, when Zr is the main target, if the pH is adjusted at a relatively high value, such as 1.4 or 1.6, Zr can be efficiently extracted.

Second Example

Production Example 4

A 1000 mL three-neck flask was charged with: 300 g (2.0 mol) of p-tert-butylphenol, 64.0 mL of diphenyl ether, and 56.0 mL (1.0 mol) of ethylene glycol; and the mixture was heated with stirring under nitrogen atmosphere. When the temperature reached 60° C., 28.0 g (0.5 mol) of calcium oxide was added; the temperature was raised up to 120° C. in about 20 minutes and then the mixture was reacted for 2 hours.

After the reaction, ethylene glycol and water produced by the reaction were evaporated under reduced pressure. A certain amount of diphenyl ether which was removed during the evaporation under reduced pressure was added and the mixture was heated with stirring again under nitrogen atmosphere. When the temperature reached 100° C., 95.9 g (3.0 mol) of sulfur was added in one portion; the temperature was raised up to 230° C. and then the mixture was reacted for 3 hours.

After the reaction, the reaction solution was allowed to cool. When the temperature was confirmed to have lowered down to 110° C., 250 mL of toluene was gradually added to the reaction mixture to reduce the viscosity; then, the diluted reaction mixture was quenched by pouring it into a 500 mL of 4N sulfuric acid.

Precipitated calcium sulfate was filtered off, and the filtrate was washed with a saturated aqueous sodium sulfate solution; then, the obtained organic phase was concentrated and heated to 80° C.

A separately prepared 1 L of acetic acid was heated at 80° C. and the concentrated reaction solution was poured thereto; then, the obtained mixture was stirred at 80° C. for about 1 hour and it was left standing overnight at room temperature.

Precipitation was washed with distilled water; then, to remove remaining acetic acid, the precipitation was dissolved in a large amount of chloroform and washed with sodium sulfate aqueous solution.

Thereafter, the organic phase was dried over sodium sulfate and concentrated; then it was dried under reduced pressure overnight. Finally, the cyclic phenol sulfide intermediate oligomer of the reaction product of the following formula was obtained.

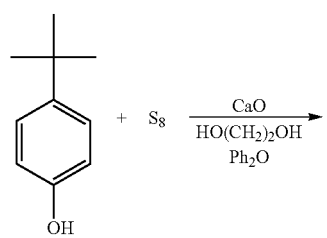

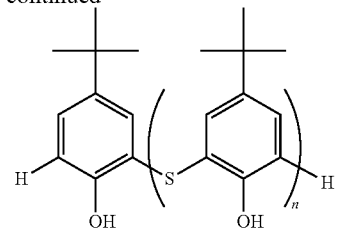

Production Example 5

A 500 mL three-neck flask was charged with: 30 g the cyclic phenol sulfide intermediate oligomer obtained in Production example 4, 64.0 mL of diphenyl ether, 3.99 g of sodium hydroxide, and 1.62 g of acetic acid, in the mentioned order; and the mixture was heated with stirring under nitrogen atmosphere. When the temperature reached 100° C., 2.14 g of sulfur was added in one portion; the temperature was raised up to 230° C. in about 1 hour and then the mixture was reacted for 4 hours.

After the reaction, the reaction mixture was allowed to cool and then quenched by pouring 100 mL of 2N sulfuric acid into the reaction mixture; then, 100 mL of n-heptane was added thereto and stirred for about 10 minutes.

Then, the mixture was washed with aqueous sodium sulfate solution to remove sulfuric acid, and the organic layer was separated. The diphenyl ether in the organic phase was evaporated under reduced pressure, and acetone was added to form precipitation.

By filtering the precipitation and drying under reduced pressure, crude crystal of the cyclic phenol sulfide shown in the following formula was obtained. By dissolving the crude crystal in chloroform and performing recrystallization, the cyclic phenol sulfide was purified.

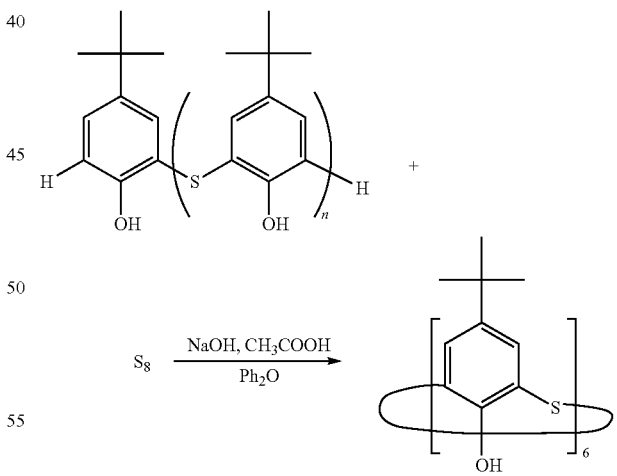

Production Example 6

A 500 mL two-neck flask was charged with: 1077.13 mg (1 mmol) of the compound obtained in Production example 5 and 2935.71 mg (9 mmol) of cesium carbonate; the atmosphere inside the flask was replaced with a nitrogen atmosphere, then, 100 mL of acetone was added and the mixture was stirred.

Thereafter, 1335 μL (12 mmol) of ethyl bromoacetate was added and stirred and heated to reflux for 3 hours.

After reaction, the reaction mixture was concentrated and the acetone was evaporated; then, to remove unreacted ethyl bromoacetate, the residue was dried at 60° C. for several hours under reduced pressure.

Then, the dried material was dissolved in about 100 mL of chloroform and washed with aqueous sodium sulfate solution three times to remove salts of byproducts.

The obtained organic phase was dried over anhydrous sodium sulfate and concentrated, and then the residue was sufficiently dried under reduced pressure so as to obtain a crude product. The crude product was purified by recrystallization from ethanol to afford the target compound shown by the reaction product of the following formula.

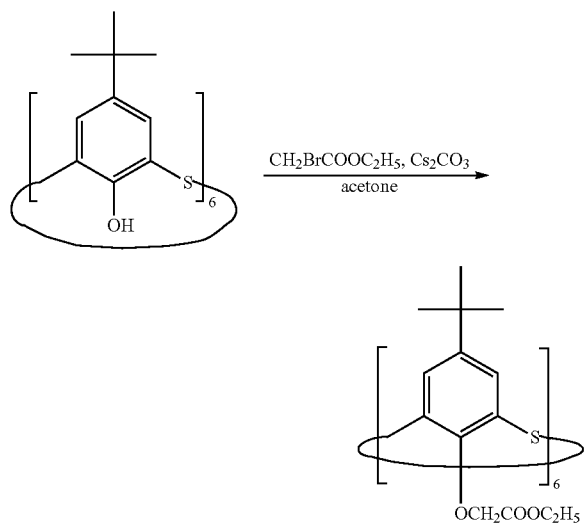

Production Example 7

A 500 mL two-neck flask was charged with: 1081.93 mg (1 mmol) of the compound obtained in Production example 5 and 1246.38 mg (9 mmol) of potassium carbonate; the mixture was stirred under nitrogen atmosphere, and then, 100 mL of acetone was added.

Thereafter, 1245 μL (12 mmol) of methyl bromoacetate was added and the mixture was stirred, and the reaction mixture was heated to reflux for 24 hours.

After reaction, the reaction mixture was concentrated and the acetone was evaporated; then, to remove unreacted methyl bromoacetate, the residue was dried at 60° C. for several hours under reduced pressure.

Then, the dried material was dissolved in about 100 mL of chloroform and washed with aqueous sodium sulfate solution three times to remove salts of byproducts. The obtained organic phase was dried over anhydrous sodium sulfate and concentrated, and then the residue was sufficiently dried under reduced pressure to afford a crude product.

The crude product was purified by recrystallization from ethanol to afford the target compound shown by the reaction product of the following formula.

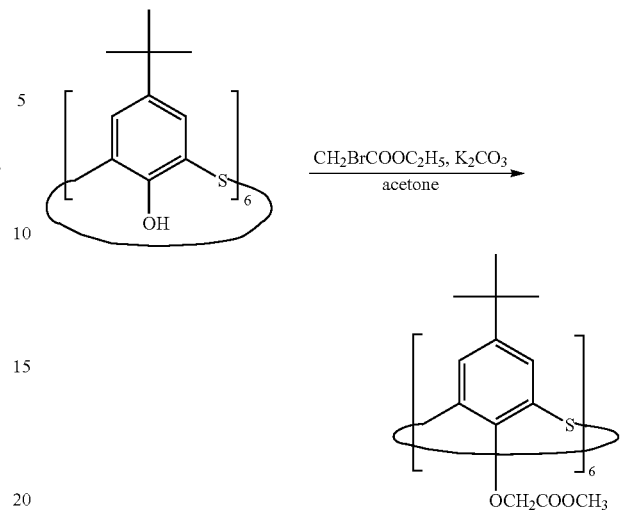

Production Example 8

A two-neck flask was charged with: 1.00 g (0.63 mmol) of the compound obtained in Production example 6, 1.10 g (27.5 mmol) of sodium hydroxide, and 250 mL of a mixed solvent of ethanol and water (3:2); and the mixture was heated to reflux for 24 hours.

After reaction, the reaction mixture was allowed to cool and then quenched in an ice bath by pouring 100 mL of 4N sulfuric acid so that the reaction solution becomes pH=1.

Thereafter, the precipitation was collected by suction filtration. Then, to remove sodium sulfate which precipitated at the same time, the collected precipitation was dissolved in acetone and filtered again for purification; finally, the target compound shown by the reaction product of the following formula was obtained.

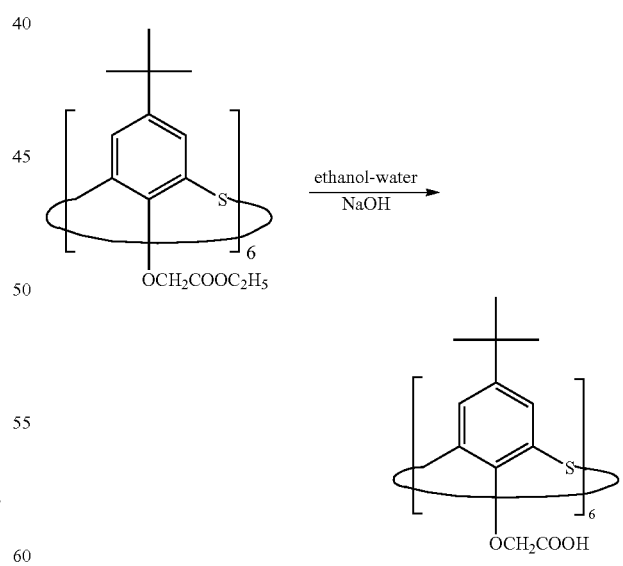

Example 2

Experiment of extracting rare metals and platinum group metals was conducted with the cyclic phenol sulfide derivatives obtained in Production examples 6 to 8.

In the extraction experiment, firstly, 50 mL of an organic phase was prepared by dissolving a cyclic phenol sulfide described above in chloroform so that the concentration was 2.92 mM; and a 50 mL of PGM (Platinum-group Metals) solution (pH: 0.8) which was obtained by preparing PGM solution (including: Rh=264.3 ppm, Pd=737.8 ppm, Pt=434.1 ppm, Zr=198.2 ppm, Ce>3840.5 ppm, Ba=2118.2 ppm, Al=2272.5 ppm, La=666.9 ppm, and Y=36.3 ppm) where platinum group metals recovered from manufacturing process of automotive catalyst, as rare metals and platinum group metals, were dissolved into a mixed solution of hydrochloric acid and aqueous hydrogen peroxide solution, and by diluting the PGM solution 50-fold with distilled water was prepared.

Then, the prepared organic phase and aqueous metal solution were filled in a 200 mL separating funnel and shaken and agitated for 30 minutes.

Thereafter, the metal concentration in the aqueous phase was analyzed by using ICP emission spectrometer, and then the extraction rate (E %) was calculated with the formula (I) according to the obtained results.

Figure 2:
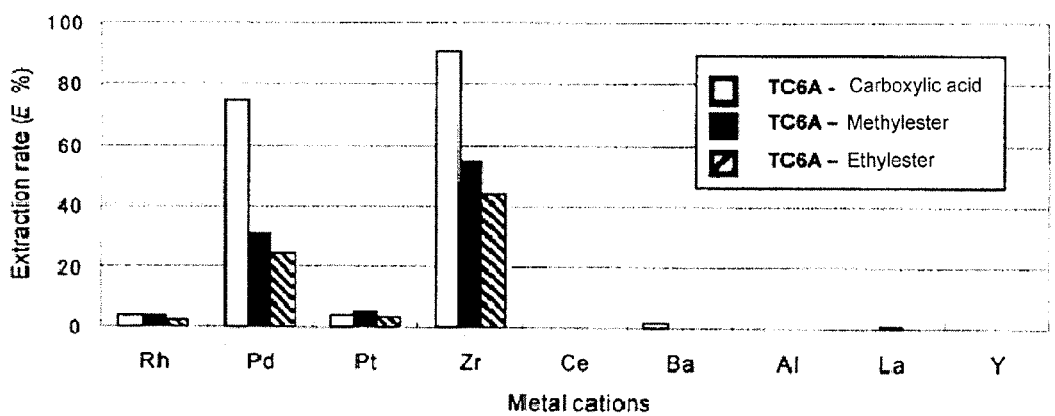
FIG. 2 is a graph showing extraction rate (E %) of Example 2.

Concentration ratio of a cyclic phenol sulfide derivative to that of metals in the aqueous solution was supposed to be a molar concentration ratio of 1:1. The extraction results are shown in FIG. 2.

According to the results, when the PGM solution was diluted 50-fold with distilled water, compared with ester adduct of Production examples 6 and 7, the carboxylic acid adduct which was obtained in Production example 8 showed higher extraction performance selectively for Pd (74%) and Zr (90%). With the carboxylic acid adduct, metals other than Pd and Zr were hardly extracted.

The ethylester adduct shown in Production example 6 showed high extraction performance selectively for particularly Pd (24%) and Zr (44%). The methylester adduct shown in Production example 7 showed high extraction performance for particularly Pd (31%) and Zr (55%).

Example 3

Experiment to extract rare metals and platinum group metals was conducted with the cyclic phenol sulfide derivative obtained in Production example 8.

In the extraction experiment, 50 mL of an organic phase was prepared by dissolving the cyclic phenol sulfide in chloroform so that the concentration was 2.92 mM; and a 50 mL of PGM (Platinum-group Metals) solution which was obtained by preparing a PGM solution (including: Rh=264.3 ppm, Pd=737.8 ppm, Pt=434.1 ppm, Zr=198.2 ppm, Ce>3840.5 ppm, Ba=2118.2 ppm, Al=2272.5 ppm, La=666.9 ppm, and Y=36.3 ppm) where platinum group metals recovered from manufacturing process of automotive catalyst, as rare metals and platinum group metals, were dissolved into a mixed solution of hydrochloric acid and aqueous hydrogen peroxide solution, and by diluting the PGM solution 50-fold with hydrochloric acid was prepared.

The prepared organic phase and aqueous metal solution were filled in a 200 mL separating funnel and shaken and agitated for 30 minutes.

Thereafter, the metal concentration in the aqueous phase was analyzed by using ICP emission spectrometer, and then the extraction rate (E %) was calculated with the formula (1) according to the obtained results.

Figure 3:
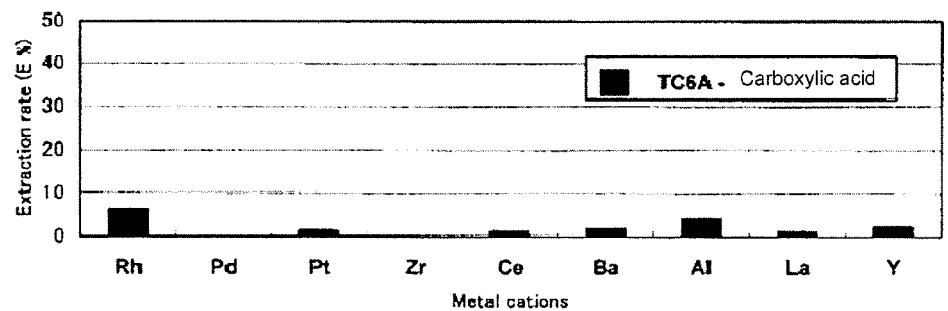
FIG. 3 is a graph showing extraction rate (E %) of Example 3.

The molarity ratio of the concentration of a cyclic phenol sulfide derivative to that of metals in the aqueous solution was supposed to be 1:1. The extraction results are shown in FIG. 3.

According to the results, when the PGM solution was diluted 50-fold with hydrochloric acid (pH: −1.0), all the metals were hardly extracted with the carboxylic acid adduct obtained in Production example 8.

Example 4

Experiment to extract rare metals and platinum group metals was conducted with the cyclic phenol sulfide derivative obtained in Production example 8.

In the extraction experiment, 50 mL of an organic phase was prepared by dissolving the cyclic phenol sulfide in chloroform so that the concentration was 2.92 mM; and 50 mL of a solution obtained by diluting, 10-fold, a standard metal solution (100 ppm) containing Rh, Pd, Pt, Zr, Ce, Ba, Al, La, and Y as rare metals and platinum-group metals with hydrochloric acid was prepared.

The prepared organic phase and aqueous metal solution were filled in a 200 mL separating funnel and shaken and agitated for 30 minutes.

Thereafter, the metal concentration in the aqueous phase was analyzed by using ICP emission spectrometer, and then the extraction rate (E %) was calculated with the formula (1) according to the obtained results.

Figure 4:
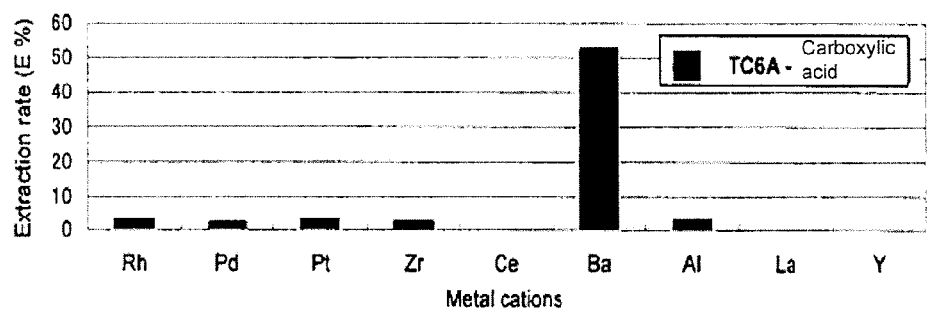
FIG. 4 is a graph showing extraction rate (E %) of Example 4.

The molarity ratio of the concentration of a cyclic phenol sulfide derivative to that of metals in the aqueous solution was supposed to be 1:1. The extraction results are shown in FIG. 4.

According to the results, when the metal solution was diluted 10-fold with hydrochloric acid (pH: −1.0), carboxylic acid adduct obtained in Production example 8 showed 50% performance in extracting Ba. However, it could hardly extract all the other metals.

(Consecutive Extraction by Changing pH)

According to the present invention, consecutive extraction of rare metals can be carried out. For example, in Example 1, firstly, Rh, Pd, and Zr are selectively dominantly extracted by extraction in a pH range of 1.2-1.6; then, Pt is selectively dominantly extracted from the solution, at pH 1.0, of which rare-metal concentration has been reduced.

(Consecutive Extraction by Changing Extractant)

An example of consecutive extraction by changing extractant is that: firstly, Pd and Zr are selectively dominantly extracted with the extractant of Example 2 (containing anyone of carboxylic acid adduct, ethylester, and methylester) under conditions of Example 2; then, Pt is selectively dominantly extracted with the extractant of Example 1 from the solution of which rare-metal concentration has been reduced. Together with the change of extractant, pH of the solution may be changed.

Comparative Example

Rare metal extraction was carried out, from a PGM aqueous solution, with both tributyl phosphate (TBP) as an extractant for solvent extraction of uranium and di(2-ethylhexyl) phosphoric acid (i.e. D2EHPA) as an extractant for e.g. rare earth, Ni, and Zr.

Except for using 50 mL organic phases obtained by diluting TBP or D2EHPA with kerosene so that concentration of each organic phase is 30 mass %, the extraction experiment was conducted in the same manner as Example 2.

Figure 5:
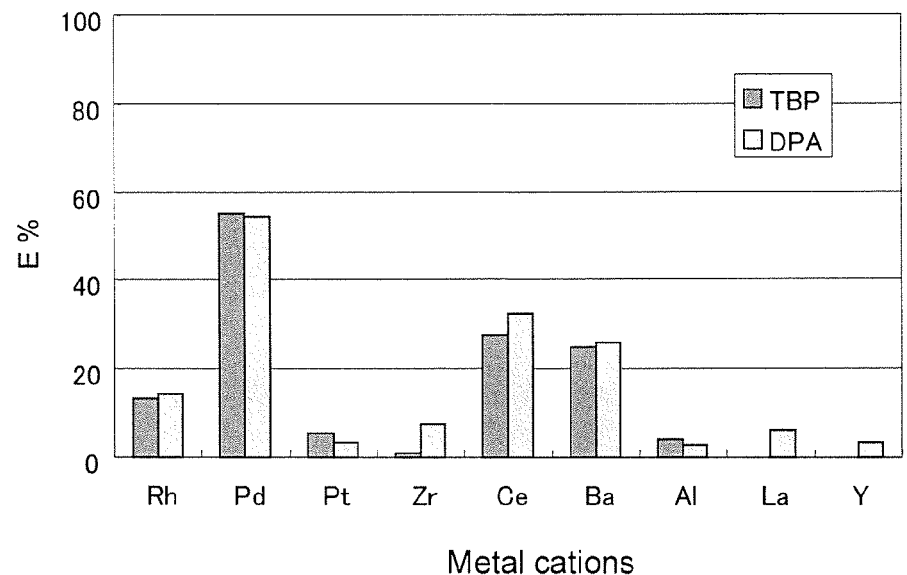
FIG. 5 is a graph showing extraction rate (E %) of the Comparative example.

The extraction results are shown in FIG. 5. According to FIG. 5, although it was observed that about 55% of Pd as well as some percentage of Ce and Ba were extracted with the conventional extractant (i.e. TBP and D2EHPA), there was no clear selectivity and high efficiency. It should be noted that D2EHPA in FIG. 5 is referred to as DPA.

The above has described the present invention associated with the most practical and preferred embodiments thereof. However, the invention is not limited to the embodiments disclosed in the specification. Thus, the invention can be appropriately varied as long as the variation is not contrary to the subject substance and conception of the invention which can be read out from the claims and the whole contents of the specification. It should be understood that the rare metal extractant and the method for consecutive extractive separation of rare metals with such an alternation are included in the technical scope of the invention.

INDUSTRIAL APPLICABILITY

By using the rare metal extractants of the present invention, certain rare metals can be extracted and separated from a rare-metal-containing aqueous solution obtained by extracting various rare metals from waste products. Those rare metals are useful for the materials of catalyst for automobile, fuel cell, and ultrahigh-strength magnet.

The invention claimed is:

1. A method for consecutive extractive separation of plural species of rare metals with a rare metal extractant containing a cyclic phenol sulfide derivative of the formula (1) from an aqueous solution containing plural species of rare metals, comprising the step of:
extracting rare metal(s) more than once by changing pH of the aqueous solution once or more depending on desired rare metal(s), to selectively dominantly extract particular rare metal(s) in each extraction process, wherein the particular rare metal(s) is/are at least one selected from the group consisting of zirconium, palladium, and platinum:

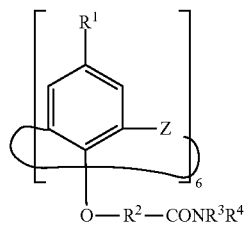

wherein in the formula (1), $R^1$ is a hydrogen atom or a $C_1$-$C_{10}$ hydrocarbon; $R^2$ is a $C_0$-$C_{10}$ hydrocarbon; $R^3$ and $R^4$ are independently a linear or branched $C_1$-$C_5$ alkyl group; and Z is one selected from the group consisting of a sulfide group, a sulfinyl group, and a sulfonyl group.

2. The method for consecutive extractive separation of plural species of rare metals according to claim 1, wherein the pH to be changed once or more includes range(s) of more than 0.8 and less than 1.2 and/or more than 1.2 and less than 1.8.

3. The method for consecutive extractive separation of plural species of rare metals according to claim 2, wherein one of the extracting steps is to selectively dominantly extract platinum.

4. The method for consecutive extractive separation of rare metals according to claim 2, comprising the steps of:
extracting palladium and platinum in a pH range of more than 0.8 and less than 1.2; and
extracting zirconium in a pH range of more than 1.2 and less than 1.8.

5. The method for consecutive extractive separation of plural species of rare metals according to claim 1, wherein one of the extracting steps is to selectively dominantly extract platinum.

6. The method for consecutive extractive separation of rare metals according to claim 1, comprising the steps of:
extracting palladium and platinum in a pH range of more than 0.8 and less than 1.2; and
extracting zirconium in a pH range of more than 1.2 and less than 1.8.

7. A method for consecutive extractive separation of plural species of rare metals, comprising the steps of:
extracting rare metal with a rare metal extractant containing a cyclic phenol sulfide derivative of the formula (1) from an aqueous solution containing plural species of rare metals; and
extracting rare metal with a rare metal extractant containing a rare metal extractant which contains a thiacalixarene other than the compound of the formula (1) from an aqueous solution containing plural species of rare metals,
to selectively dominantly extract particular rare metal(s) in each step, wherein the particular rare metal(s) is/are at least one selected from the group consisting of zirconium, palladium, and platinum:

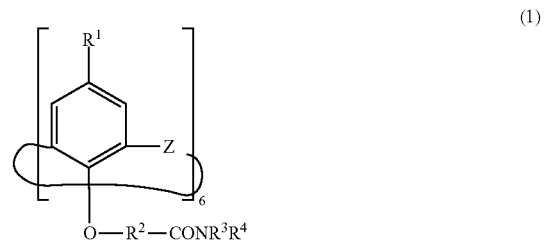

wherein in the formula (1), $R^1$ is a hydrogen atom or a $C_1$-$C_{10}$ hydrocarbon; $R^2$ is a $C_0$-$C_{10}$ hydrocarbon; $R^3$ and $R^4$ are independently a linear or branched $C_1$-$C_5$ alkyl group; and Z is one selected from the group consisting of a sulfide group, a sulfinyl group, and a sulfonyl group.

8. The method for consecutive extractive separation of plural species of rare metals according to claim 7, wherein the rare metal extractant which contains a thiacalixarene other than the compound of formula (1) is a rare metal extractant containing a thiacalixarene of the formula (2):

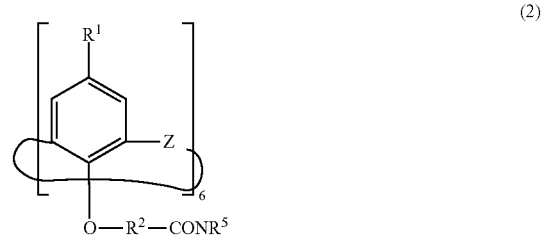

in the formula (2), $R^1$ and $R^5$ are independently a hydrogen atom or a $C_1$-$C_{10}$ hydrocarbon; $R^2$ is a $C_0$-$C_{10}$ hydrocarbon; and Z is one selected from the group consisting one of a sulfide group, a sulfinyl group, and a sulfonyl group.

9. The method for consecutive extractive separation of plural species of rare metals according to claim 8, wherein one of the extracting steps is to selectively dominantly extract platinum.

10. The method for consecutive extractive separation of rare metals according to claim 8, wherein $R^5$ in the formula (2) is a $C_1$-$C_5$ hydrocarbon.

11. The method for consecutive extractive separation of rare metals according to claim 8, wherein, first palladium and zirconium are selectively extracted with the rare metal extractant containing a thiacalixarene of the formula (2); and, secondly, platinum is selectively extracted with the rare metal extractant containing a cyclic phenol sulfide derivative of the formula (1).

12. The method for consecutive extractive separation of plural species of rare metals according to claim 7, wherein one of the extracting steps is to selectively dominantly extract platinum.

* * * * *